United States Patent [19]

Almér et al.

[11] 4,190,380
[45] Feb. 26, 1980

[54] DEVICE IN CONCRETE BLOCKS

[76] Inventors: Bengt Ö. Almér, Saltholmsgatan 5, Vastra Frolunda, Sweden, S-421 76; Karl G. Gidlöf, Sjögängen 28, Västra Frolunda, Sweden, S-421 71

[21] Appl. No.: 967,689

[22] Filed: Dec. 8, 1978

[30] Foreign Application Priority Data

Dec. 12, 1977 [SE] Sweden ............................ 7714053
Oct. 27, 1978 [SE] Sweden ............................ 7811174

[51] Int. Cl.² ............................................. E01F 15/00
[52] U.S. Cl. ............................................................ 404/6
[58] Field of Search ................... 404/6, 7, 12, 13, 14, 404/40, 41, 37; 52/583, 587; 256/13.1

[56] References Cited

U.S. PATENT DOCUMENTS

| | | | |
|---|---|---|---|
| 1,264,582 | 4/1918 | Vergara | 52/583 X |
| 3,065,680 | 11/1962 | Wiedman | 404/6 |
| 3,092,371 | 6/1963 | Knudsen | 404/6 X |
| 3,372,519 | 3/1968 | Russell | 52/587 X |
| 3,678,815 | 7/1972 | Yonker | 404/6 |
| 3,980,279 | 9/1976 | Bofinger | 256/13.1 |
| 4,059,362 | 11/1977 | Smith | 404/6 |
| 4,089,615 | 5/1978 | Almer | 404/6 |
| 4,113,400 | 9/1978 | Smith | 404/6 |

Primary Examiner—Nile C. Byers, Jr.
Attorney, Agent, or Firm—Newton, Hopkins & Ormsby

[57] ABSTRACT

An arrangement in concrete blocks which are intended to be positioned end-to-end to form barriers for e.g. roadways and parking lots. The concrete blocks have an elongate shape with an essentially triangular cross-sectional configuration with rounded side walls, and are interconnected by means of T-shaped metal pieces, the latter being secured in the end faces of the blocks during the casting thereof and formed with cross-bars, the interconnection of the blocks being effected in that two such cross-bars at adjoining end faces of two concrete blocks positioned end-to-end are enclosed by a tubular member, whereby the blocks are locked together. The blocks may be provided with a device widening their upper part and increasing the ability of the block to guide vehicles safely back to the roadway.

14 Claims, 19 Drawing Figures

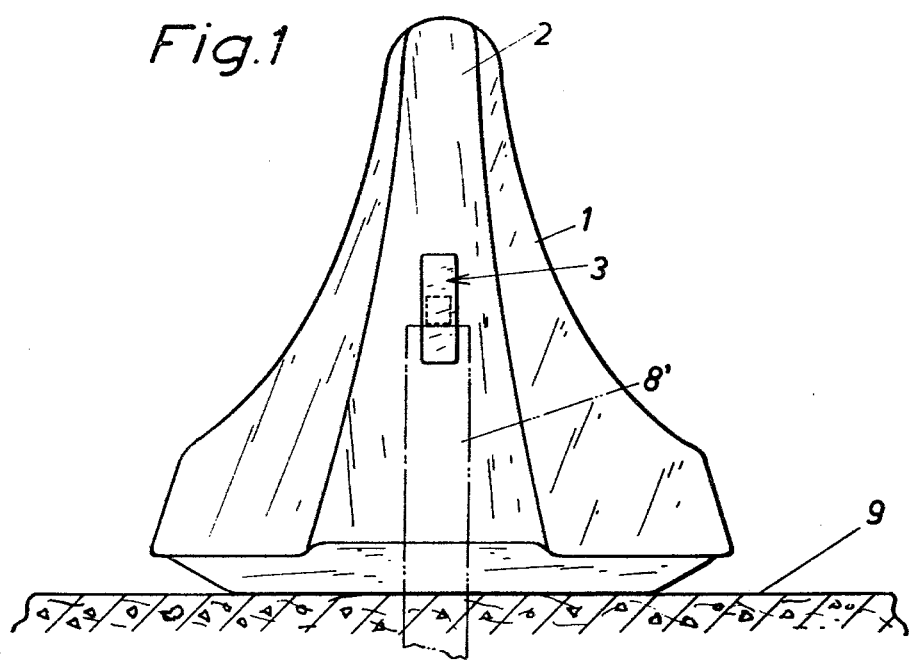
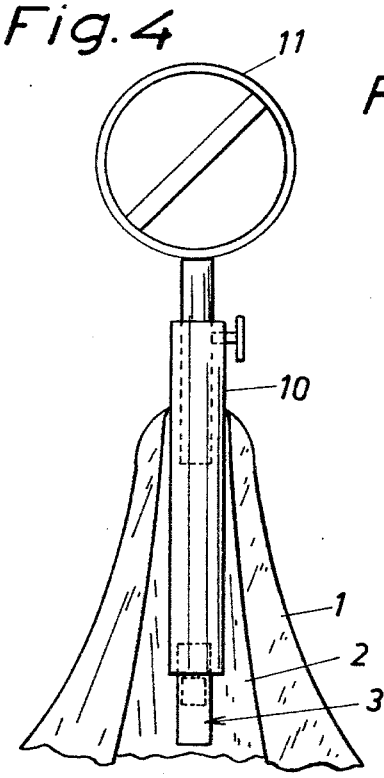
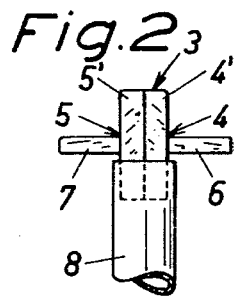
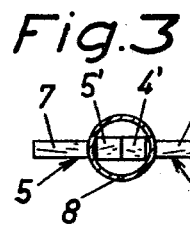

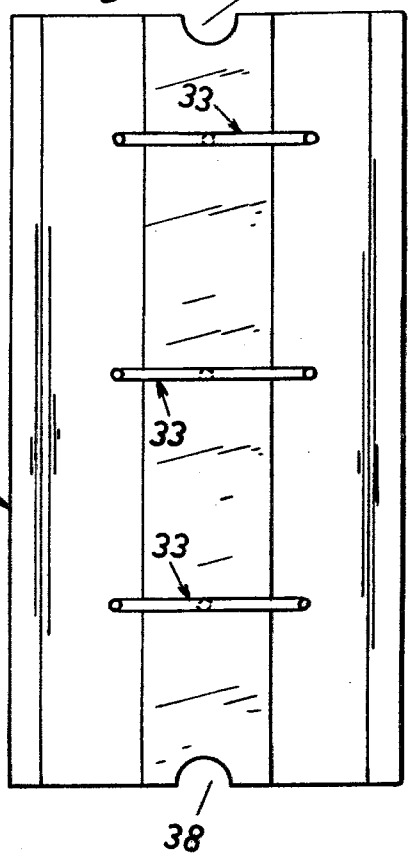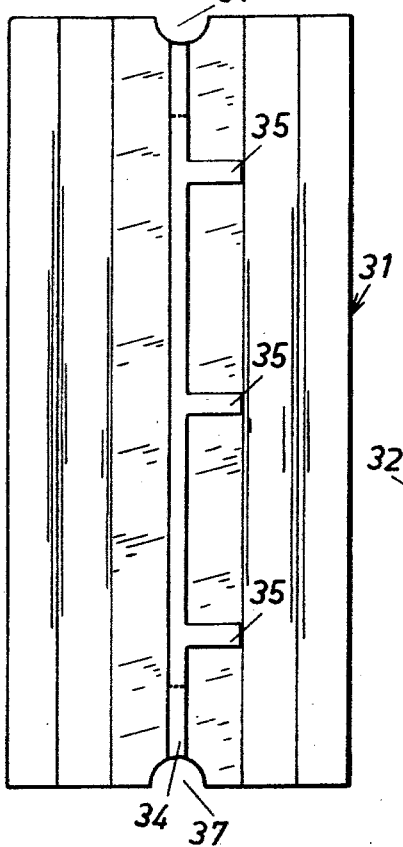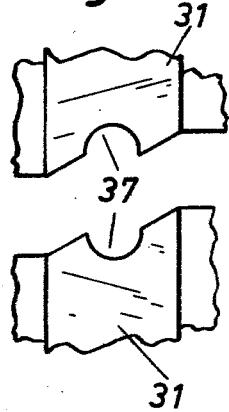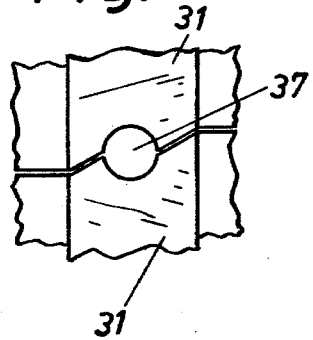

Fig.19
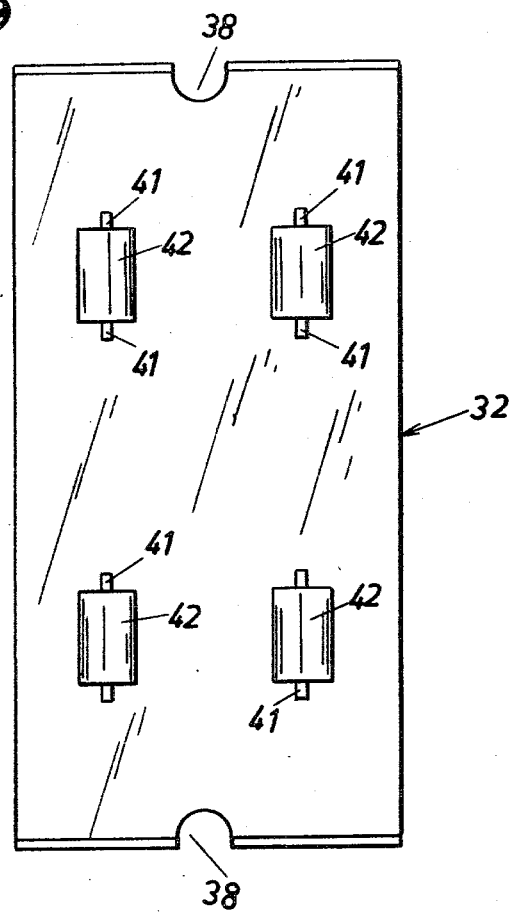
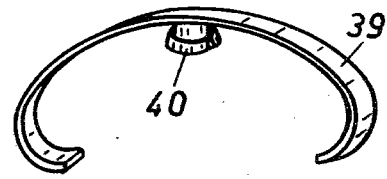
Fig.18
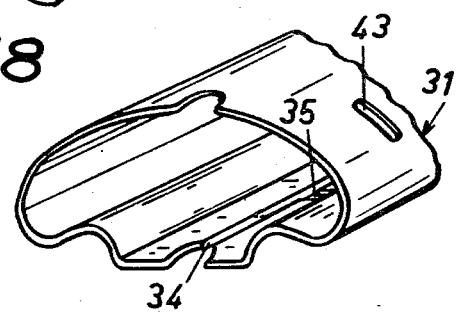

DEVICE IN CONCRETE BLOCKS

BACKGROUND OF THE INVENTION

The invention concerns a device in concrete blocks which are intended to be interconnected in end-to-end positions to delimit roadways, parking lots and similar enclosed areas, and which concrete blocks are intended to guide vehicles that leave the roadway back to their normal driving path while ensuring that any damage that might be caused to the vehicle is as slight as possible and also that the vehicle is not guided over to the side of the roadway of oncoming traffic.

Devices used to interconnect concrete blocks of the kind referred to must be such as to allow the blocks, when they are placed in position, to be easily interconnected and also, when needed, be easily disconnected, as this saves labour and therefore considerable costs.

SUMMARY OF THE INVENTION

To obtain these aims the subject invention is characterised by a coupling element positioned at each end of the block and consisting of an essentially T-shaped metal piece which is cast into the block, the cross-bar of said T-shaped piece extending in parallel with the associated end face of the concrete block and arranged, jointly with a smaller cross-bar of a coupling element secured in the end face of the adjacent concrete block, to be enclosed by a tube, whereby the two blocks are locked together.

The element in accordance with the invention may be arranged in a preferably semi-circular notch formed substantially centrally in the end face of the concrete block.

In accordance with another aspect of the invention an interconnection element of the kind referred to may be positioned in the vicinity of the lower, bevelled face of the block, i.e. the outer part of the block. In this case, the blocks may be essentially hollow, which makes it possible to suspend the concrete blocks in carrier rods. A number of various suspension arrangements are feasible for this purpose. In addition, the block may be formed with one single (side wall) only. In the latter case, the block preferably is fitted with a balance weight ensuring correct position of the block.

Furthermore, in accordance with another aspect of the subject invention it is possible to form single-wall blocks in such a manner that their suspension part, i.e. their upper part, is provided with notches into which may be inserted corresponding projections formed on the upper part of an identical single-wall block, whereby two such single-wall blocks together form a block assembly.

One has found that when a vehicle hits a concrete block at certain speeds and angles of attack, it could occasionally happen that the vehicle passes over the concrete block. This risk, however limited, is eliminated by the subject invention in accordance with one embodiment thereof which is characterised by a bulb rail which is intended to be applied on the top face of the concrete block and which improves the ability of the concrete block to guide a vehicle that drives up onto the concrete block side, with regard to returning the vehicle to its normal driving path, by softly rounding and widening the upper part of the concrete block.

The above as well as additional characteristics of the invention will appear from the appended claims.

BRIEF DESCRIPTION OF THE DRAWINGS

The invention will be described in closer detail in the following with reference to the accompanying drawings, wherein FIG. 1 is an end view of a concrete block incorporating a coupling element in accordance with the teachings of the invention, FIGS. 2 and 3 illustrate the coupling element proper in views from the side and from below, respectively, FIG. 4 shows a particular embodiment of the coupling element, FIG. 14 is a view from above of the concrete block of FIG. 7, FIG. 15 illustrates the bulb rail in a view from below, FIGS. 16 and 17 illustrate the joint between two bulb rails of the embodiment in accordance with FIG. 13, FIG. 18 illustrates a clamping member to be applied above the joint between two adjoining bulb rail ends, and FIG. 19 is a view from below of a concrete element in accordance with a still further embodiment.

DETAILED DESCRIPTION OF PREFERRED EMBODIMENTS

Figure 5:
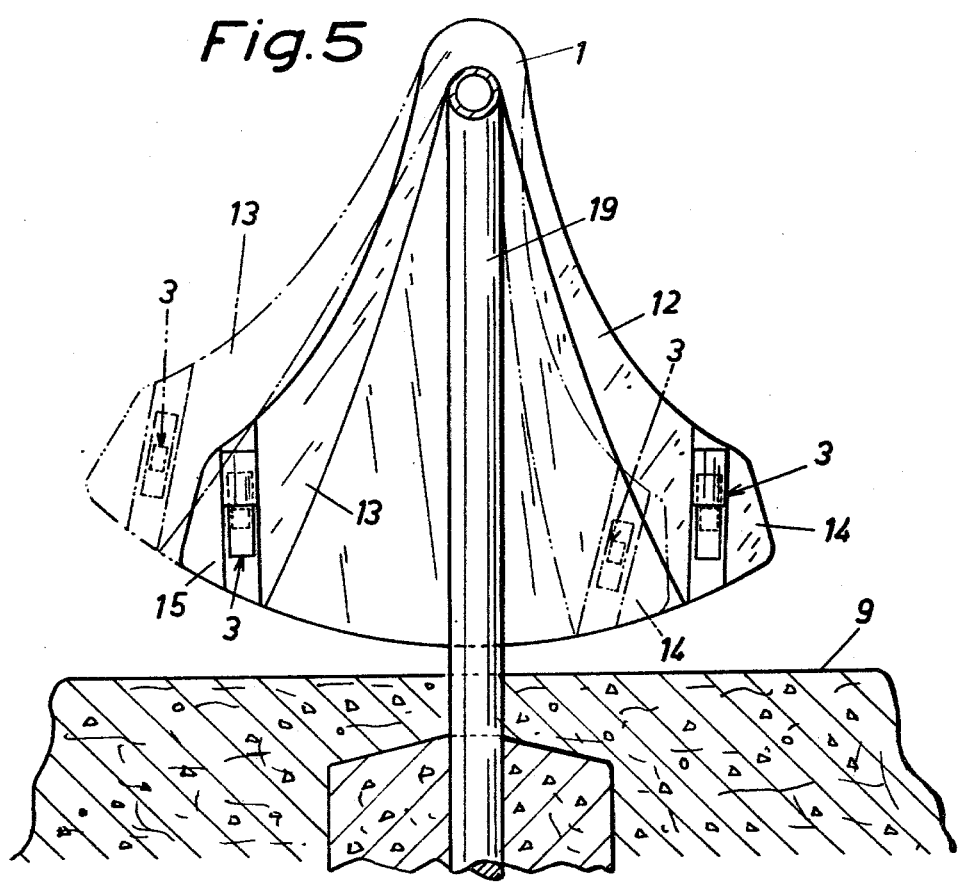
FIG. 5 shows two coupling elements used with a special embodiment of the concrete block.

FIG. 1 illustrates a solid concrete element 1 in an end view from which appears that the end face of the block 1 is formed with a recess or notch 2 in which is arranged a coupling element 3 in accordance with the invention.

FIG. 2 illustrates the coupling element 3 in accordance with the invention in a lateral view, the element as illustrated comprising two T-shaped sections 4, 5 with legs 6, 7. The legs 6, 7 (see also the plan view of FIG. 3) are intended to be secured in the concrete block 1 by being embedded therein during the casting of the block in such a manner that the cross-bars 4', 5' of the T-shaped sections, which cross bars extend at right angles to the legs 6, 7, will be positioned opposite one another, when two concrete blocks are positioned essentially end-to-end. A tube 8 is then used to lock the two vertical cross-bars 4', 5' to one another. For this purpose it is also possible to use a tube 8' which, as indicated in FIG. 1, is anchored to the ground 9, although naturally it is also possible to pass a tube 10 into the recess 2 from above, as indicated in FIG. 4. In the latter case, the tube 10 may be utilised as a support of e.g. signs, such as a road sign 11.

As illustrated in FIG. 5, the concrete block 1 may be made hollow, however with sufficient thickness of the side walls 12, 13 to ensure adequate strength of the block. In addition, care must taken to ensure that the base portions 14, 15 of the walls 12, 13 are sufficiently thick to house a coupling element 3 in accordance with the invention, one such element being inserted in the manner indicated in a suitable semi-circular notch in each one of the end walls of the block 1.

Figure 6:
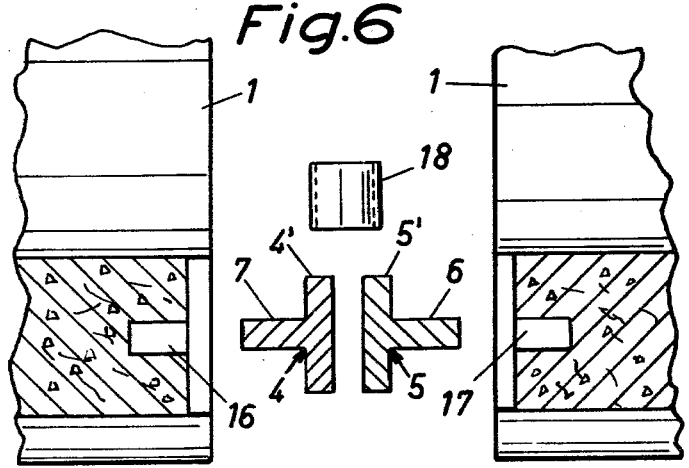
FIG. 6 is an exploded view of a coupling element in accordance with the invention.

FIG. 6 illustrates the coupling element proper on an enlarged scale and in an exploded view, the legs 6, 7 of the T-shaped sections 4, 5 intended to be cast into the blocks 1 in notches 16, 17 formed therein in such a manner that upon interconnection of two blocks placed in end-to-end positions, the T-shaped sections 4, 5 will assume the positions indicated in FIG. 2. When two blocks are placed in end-to-end positions and the coupling elements thus assume the position illustrated in FIG. 2, the latter may easily be interconnected by a tubular piece 18 which is passed over the vertically directed cross-bars 4', 5' of the T-shaped sections 4, 5.

Blocks 1 interconnected in the manner indicated in FIG. 5, i.e. at their base portions may be suspended in rods 19 anchored in the ground 9 and when interconnected by means of coupling elements in accordance with the invention the blocks will be slightly tiltable.

Figure 7:
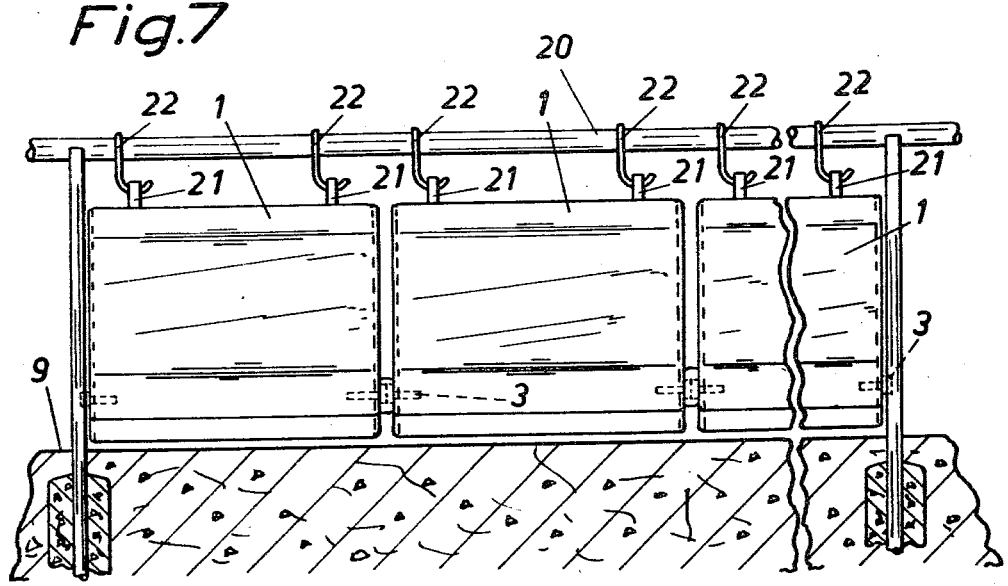
FIG. 7 is a lateral view of concrete blocks in suspended position and interconnected in accordance with the teachings of the invention.

FIG. 7 illustrates blocks 1 which are suspended from a rod 20 by means of a suspension arrangement which differs from the one illustrated in FIG. 5. In this case the blocks are provided with loops 21 by means of which the block may be suspended in hooks 22 arranged on the rod 20, the latter being anchored in the ground 9 by means of vertical rods.

Figure 8:
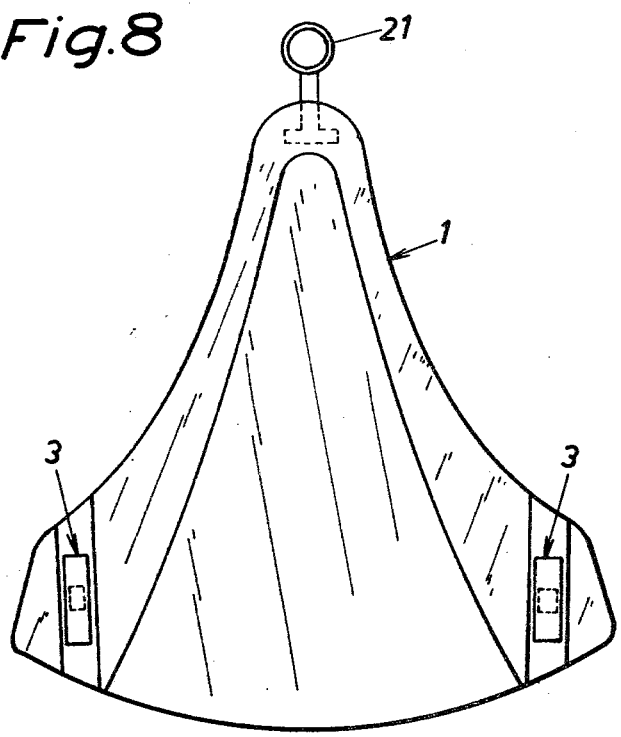
FIG. 8 is an end view of one of the blocks of FIG. 7.

FIG. 8 illustrates in end view a block 1 including a loop 21 and coupling elements 3. Also in this case the resulting barrier is somewhat yieldable.

Figure 9:
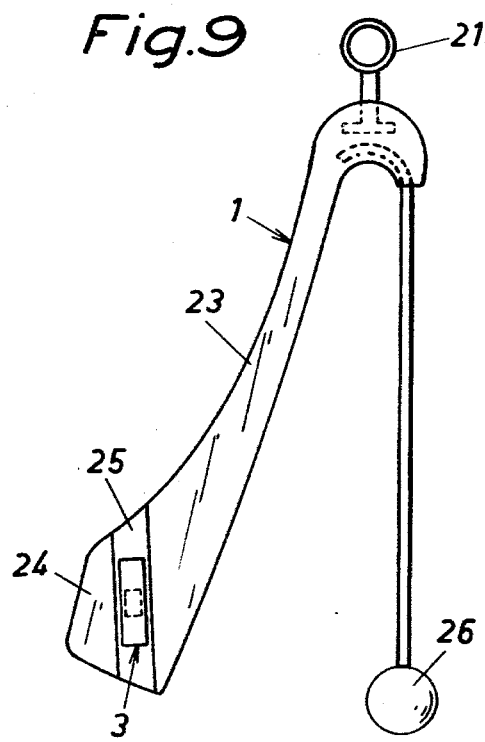
FIG. 9 is an end view of a further embodiment of the block in accordance with the invention.

In some cases it may be desirable that the concrete block projects to one side only and one example of a block of this kind is illustrated in FIG. 9, this Figure showing an end view of a block 1 formed with one single side wall 23 the base portion 24 of which is formed with a recess 25 for introduction thereinto of a coupling element 3 in accordance with the invention. This block 1 is provided with a loop 21 for suspension in the manner described with reference to FIG. 7. To ensure that the block assumes the desired position it is preferably formed with a balance weight 26. The upper part of the block may have the configuration indicated in FIG. 10, which makes it possible, by arranging two blocks in mirror-image position, to interconnect the blocks 1, placing notches and projections formed at the upper part thereof in interdigited positions, whereby when two such blocks are interconnected a combined block is obtained, having essentially the appearance illustrated in FIG. 8.

Figure 11:
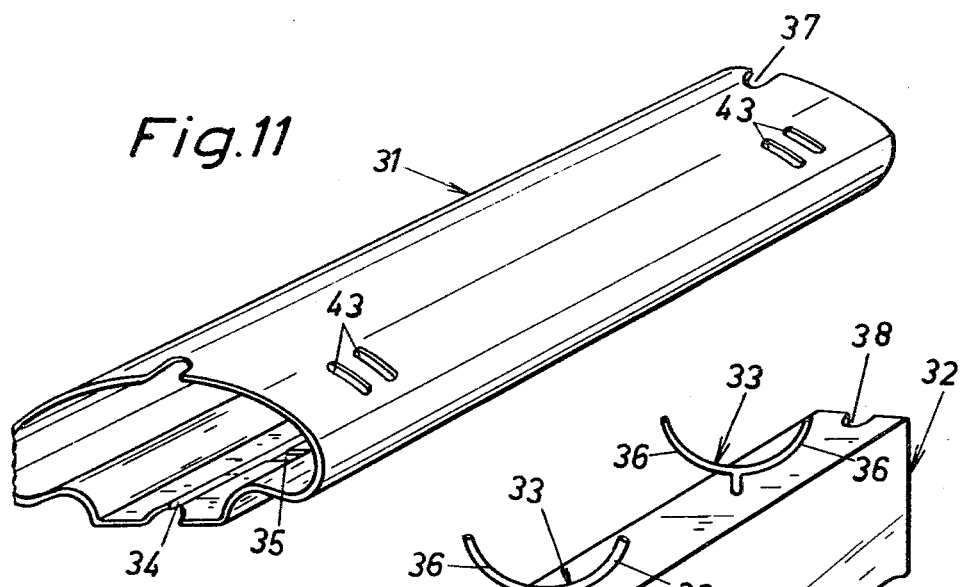
FIG. 11 is a perspective view of a particular embodiment of a bulb rail intended to be used with a particular embodiment of the concrete block in accordance with the invention.
Figure 12:
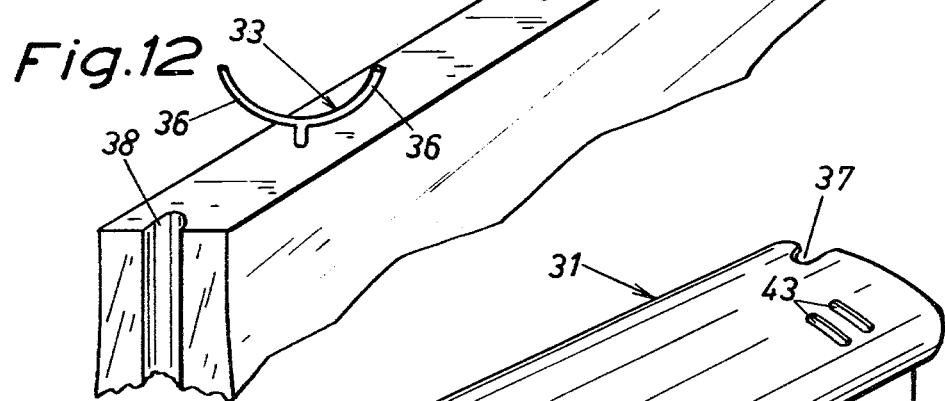
FIG. 12 illustrates the upper part of a concrete block in accordance with this embodiment.
Figure 13:
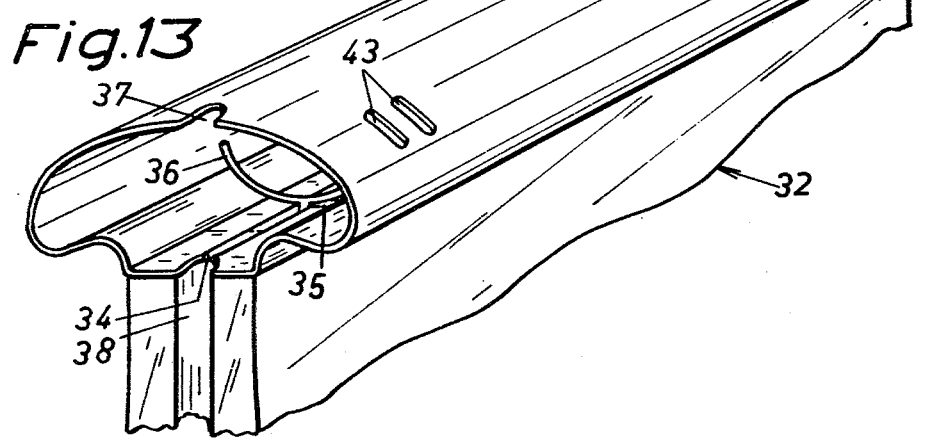
FIG. 13 illustrates the bulb rail in applied position.

In accordance with one aspect of the invention illustrated in FIG. 11 a bulb rail 31 is provided, which may be formed by bent or extruded sheet metal or plastics. FIG. 12 illustrates the upper part of a concrete block 32 on the upper face of which the bulb rail 31 is intended to be applied. For this purpose the block 32 is provided with retainers 33 intended for insertion into grooves 34 or 35 formed in the bulb rail. In the case of the groove 34 the bulb rail 31 need only be slided endwise to the desired position whereas in the case of the grooves 35, the bulb rail is passed over the retainers 33 and is then slid lengthwise to the desired position. The arms 36 of the retainers 33 are designed to press resiliently against the inner face of the bulb rail 31 in such a manner that the latter is secured in position against the upper face of the concrete block 32.

In FIGS. 14 and 15 are shown the surfaces of respectively the bulb rail 31 and the concrete block 32 that are to be attached to one another. Although FIG. 15 shows grooves 34 as well as grooves 35 it should be obvious to the expert in the field that when the bulb rail 31 is formed with the grooves 35 the groove 34 need only be shaped to allow slight displacement of the bulb rail 31, allowing the arms 36 on the retainers 33 to press against the inner face of the bulb rail 31 adjacent the grooves 35. Obviously there is nothing to prevent designing the bulb rail 31 in the manner indicated in FIG. 15, if such a combination were preferable.

FIGS. 16 and 17 show the ends of the bulb rail 31. As indicated in the drawings, these ends are biased and preferably non-symmetrical in order to prevent vehicles that drive up onto the concrete block from catching in this edge. In this connection should be pointed to the provision of an opening 37, corresponding to the notches 38 in the end faces of the concrete block 32 and intended to house and retain e.g. rods carrying traffic or road signs and the like. In this connection deserves mentioning also that the hollow bulb rail 31 makes it possible to draw electrical wiring and cables therein in a safe and protected position to road signs that should be illuminated.

In FIG. 18 is shown a clamping member 39, made from sheet metal or plastics, intended to be clamped over the joint between two bulb rails 31 placed in end-to-end position and to be retained in this position by its inherent resiliency. The clamping member 39 is provided with a pin stub 40 intended to be inserted in the opening 37, e.g. through clamping action.

FIG. 19, finally, shows a concrete block 32 which is provided on its lower face with shafts 41 supporting rollers 42 whereby displacement of the block 32 is facilitated. On account of the immobilising effect obtained through the bulb rails 31 applied on the upper face of the block 32, which bulb rails need not have an even length with the concrete block 32, the blocks 32 may be fitted with these rollers 42 which facilitate displacement of the block, particularly in the non-interconnected position thereof. Prior-art blocks have required provision thereon of leg sections, making it possible to insert the fork members of e.g. a forklift truck underneath the block in order to move the block.

The bulb rail 31 could of cause be given many other shapes than the one illustrated, provided it prevents cars from passing over the concrete block and onto the roadway at the opposite side of the block. In addition, the rail should have a configuration that eliminates the tendencies of the car to wobble and it should guide the car softly back onto the roadway. Without detailed explanations it should be obvious to the expert that a variety of shapes of the bulb rail could serve this purpose. In addition, the bulb rail 31 is preferably provided with apertures 43 in which could be applied e.g. lamps. Rubber pads could be inserted intermediate the end faces of adjoining blocks, if desired.

The invention is not limited to the embodiments as shown and described but various modifications are possible within the scope of the appended claims.

We claim:

1. An improvement in concrete blocks of the kind intended to be interconnected in end-to-end positions to form barriers for delimitation of roadways, parking lots and similar enclosed areas, said blocks having an essentially triangular cross-section configuration and an elongate shape, the improvement comprising a coupling element positioned at each end of said block, said element consisting of an essentially T-shaped metal piece cast into said block, the cross-bar of said T-shaped metal piece extending in parallel with the end face of said concrete block, said cross-bar arranged, jointly with a similar cross-bar of a coupling element positioned in the end face of the adjoining concrete block, to be enclosed by a tube, thus locking together said two blocks positioned end-to-end.

2. An improvement as claimed in claim 1, comprising a preferably semi-circular notch formed in each end face of said block, the leg of the associated T-shaped metal piece secured in said notch.

3. An improvement as claimed in claim 1, wherein said concrete block is hollow, the walls of said concrete block formed with increasing thickness in the direction downwards so as to ensure that the bases of said block have sufficient thickness to house coupling elements therein.

4. An improvement as claimed in claim 3, comprising a supporting stand consisting of elongate members such as e.g. tubes and rods, and preferably anchored to the ground, the upper part of said block being reinforced so as to allow said block to be tiltably suspended in said stand.

5. An improvement as claimed in claim 4, wherein loops are provided on the upper part of said block, said loops arranged to be suspended in hooks secured in said supporting stand.

6. An improvement as claimed in claim 1, said block comprising a side wall, and an upper part, a balance weight attached to said upper block part (FIG. 9).

Figure 10:
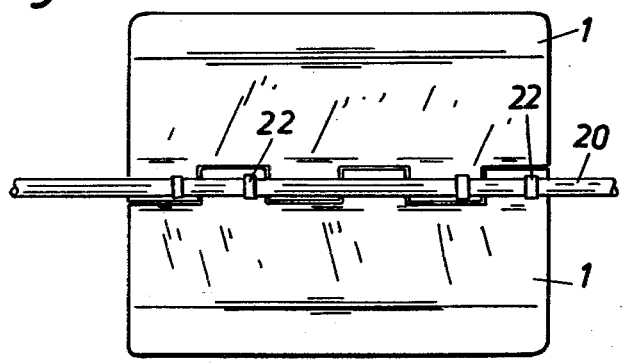
FIG. 10 is a plan view of two blocks in accordance with FIG. 9 when interconnected in a mirror-image position.

7. An improvement as claimed in claim 6, comprising notches at the upper part of said block, said notches receiving therein projections formed on a block placed in mirror-image position (FIG. 10).

8. An improvement as claimed in claim 1, comprising a bulb rail to be applied on the upper face of said concrete block, said bulb rail designed to softly round and widen the upper part of said concrete block, thus improving the capacity of said block to guide a vehicle driving up a side of said block, with regard to returning said vehicle back to its normal roadway.

9. An improvement as claimed in claim 8, wherein said bulb rail is a hollow sheet metal border, secured to said concrete block by means of retainers, said retainers anchored in said concrete block and formed with laterally extending, resilient arms, apertures formed in the lower face of said bulb rail, said retainer arms arranged to be inserted through said apertures and thus be introduced into the interior of said bulb rail to secure the latter to said block by pressing said bulb rail against the upper face of said concrete block.

10. An improvement as claimed in claim 8, wherein the end faces of said bulb rail are non-symmetrical to prevent engagement thereof by a vehicle.

11. An improvement as claimed in claim 8, wherein the length of said bulb rail differs from that of the concrete block.

12. An improvement as claimed in claim 8, wherein apertures are formed in said bulb rail, said apertures intended to serve as lamp attachments.

13. An improvement as claimed in claim 8, comprising a strap of plastics, metal or the like, said strap intended to be pressed over the joint between two adjoining bulb rails.

14. An improvement as claimed in claim 8, comprising shafts provided at the lower face of said concrete block, said shafts supporting rollers serving to facilitate displacement of said concrete block.

* * * * *